United States Patent
Ting et al.

(10) Patent No.: US 12,174,969 B2
(45) Date of Patent: *Dec. 24, 2024

(54) CONTINUOUS RISK ASSESSMENT FOR ELECTRONIC PROTECTED HEALTH INFORMATION

(71) Applicants: David M. T. Ting, Sudbury, MA (US); Sean Ting, San Francisco, CA (US)

(72) Inventors: David M. T. Ting, Sudbury, MA (US); Sean Ting, San Francisco, CA (US)

(73) Assignee: Tausight, Inc., Sudbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/089,646

(22) Filed: Dec. 28, 2022

(65) Prior Publication Data

US 2023/0134122 A1    May 4, 2023

Related U.S. Application Data

(63) Continuation of application No. 16/841,232, filed on Apr. 6, 2020, now Pat. No. 11,625,488.

(60) Provisional application No. 62/829,695, filed on Apr. 5, 2019.

(51) Int. Cl.
    *G06F 21/57*     (2013.01)
    *G06F 21/70*     (2013.01)
    *G16H 10/60*     (2018.01)

(52) U.S. Cl.
    CPC ............ *G06F 21/577* (2013.01); *G06F 21/70* (2013.01); *G16H 10/60* (2018.01)

(58) Field of Classification Search
    CPC ........ G06F 21/577; G06F 21/70; G16H 10/60
    See application file for complete search history.

(56) References Cited

U.S. PATENT DOCUMENTS

| | | | |
|---|---|---|---|
| 5,971,597 A * | 10/1999 | Baldwin | H05B 47/18 340/567 |
| 10,754,701 B1 * | 8/2020 | Wagner | G06F 9/5077 |
| 2007/0143851 A1 * | 6/2007 | Nicodemus | H04L 63/1433 726/4 |
| 2008/0319999 A1 | 12/2008 | Simpson et al. | |
| 2009/0024627 A1 * | 1/2009 | King | G06F 21/577 707/999.009 |
| 2011/0213774 A1 | 9/2011 | Buurman et al. | |
| 2013/0055387 A1 | 2/2013 | Kim et al. | |
| 2016/0182565 A1 * | 6/2016 | Salvador | H04L 63/08 726/1 |
| 2016/0241573 A1 * | 8/2016 | Mixer | H04L 63/20 |
| 2017/0185438 A1 * | 6/2017 | Thomas | G06F 9/45558 |
| 2018/0191770 A1 * | 7/2018 | Nachenberg | H04L 63/1441 |
| 2018/0288119 A1 * | 10/2018 | Lee | H04L 67/131 |
| 2019/0370106 A1 | 12/2019 | Boutnaru | |

(Continued)

*Primary Examiner* — Meng Li
(74) *Attorney, Agent, or Firm* — Morgan, Lewis & Bockius LLP

(57) ABSTRACT

Methods and systems for continuously and quantitatively assessing the risk to data confidentiality, integrity, and availability on identified on endpoints, servers, medical devices, and "Internet of things" devices in a networked healthcare environment monitor resource requests by user applications running on the various device. A map of resource usage by each application may be generated. Based on the map and a risk model (e.g., the contents of a risk database), application events associated with risks are detected and resources vulnerable to the risk may be identified.

22 Claims, 6 Drawing Sheets

(56) References Cited

U.S. PATENT DOCUMENTS

| | | |
|---|---|---|
| 2019/0378611 A1 | 12/2019 | Kim et al. |
| 2020/0159951 A1* | 5/2020 | McDonald ............. G06F 21/54 |
| 2020/0274777 A1 | 8/2020 | Liu et al. |
| 2020/0320203 A1* | 10/2020 | Ting ..................... G06F 21/577 |

* cited by examiner

CONTINUOUS RISK ASSESSMENT FOR ELECTRONIC PROTECTED HEALTH INFORMATION

RELATED APPLICATION

This application is a continuation of U.S. patent application Ser. No. 16/841,232, filed Apr. 6, 2020, which claims the benefit of and priority to U.S. Provisional Application No. 62/829,695, filed on Apr. 5, 2019, the entire disclosure of each of which is hereby incorporated herein by reference.

TECHNICAL FIELD

In various embodiments, the present invention relates generally to the detection and remediation of anomalous behavior in distributed, heterogeneous computational environments.

BACKGROUND

Electronic protected health information (ePHI) is central to patient care delivery. It serves not only as a longitudinal record of the patient's medical history but also increasingly for controlling medical devices used in care delivery. The Health Insurance Portability and Accountability Act of 1996 (HIPAA) requires appropriate administrative, physical and technical safeguards to ensure confidentiality, integrity and availability (CIA) for ePHI. To demonstrate compliance, the Office for Civil Rights (OCR) requires provider organizations to preserve the results of an annual Security Risk Assessment (SRA) that documents how ePHI risks are accounted for and handled within the organization. Maintaining CIA for ePHI is difficult given the ephemeral nature of ePHI, since virtually any electronic document that allows a patient to be identified is classified as PHI.

A static risk assessment such as the SRA, while useful for demonstrating compliance at a point in time, is unable to keep up with the dynamics of how ePHI can be created and distributed in a digital world. Since an up-to-date risk assessment forms the basis of effective risk mitigation, what is needed in today's networked and distributed care delivery systems is continuous risk assessment of ePHI CIA.

SUMMARY

Embodiments of the present invention involve methods and systems for continuously and quantitatively assessing the risk to CIA for ePHI identified on endpoints, servers, medical devices, and "Internet of things" (IoT) devices (hereafter, collectively, "devices" or "nodes") in a networked healthcare environment. Resource requests by user applications running on a device are monitored in order to generate a map of resource usage by each application. Based on the map and a risk model (e.g., the contents of a risk database), application events associated with risks are detected and resources vulnerable to the risk may be identified.

As used herein, the term "application" means any running process on a computational device, and in a medical setting can include healthcare information (e.g., EMR) and workflow (e.g., CPOE) systems as well as conventional software such as word processors, spreadsheets, and browsers.

In one aspect, the invention pertains to a computational system comprising, in various embodiments, a processor, an operating system, a computer memory, a plurality of user applications executing as running processes on the processor, and a risk database. The system further includes at least one agent executable by the processor and configured to (i) monitor resource requests by the user applications and, based thereon, generate a map of resource usage by each application; (ii) based on the map and the risk database, detect application events associated with risks; and (iii) upon detection of an event corresponding to a risk, determine a set of resources vulnerable to the risk and, based thereon, take an action. The action may, for example, be issuing an alert to a supervisory node responsible for the determined set of resources or updating a computational system-wide risk model. The system may, for example, be an endpoint device in an institutional network. The system may include an independent sensor associated with each of the user applications or a single sensor responsible for all of the user applications. In some embodiments, the system is a server hosting user applications for multiple endpoint devices and users, and may include an independent sensor associated with each of the user applications. For example, each of the user applications may be hosted for multiple simultaneous user sessions, and the system may include a single sensor responsible for all of the user applications.

In various embodiments, the system may include a vulnerability database and the agent may be further configured, upon detection of an application event associated with risk, to check the event against a minimum cut set of vulnerabilities stored in the vulnerabilities database.

In another aspect, the invention pertains to a method of detecting and responding to computational risks in a computational system comprising a processor, an operating system, a computer memory, and a plurality of user applications. In various embodiments, the method comprising the steps of monitoring resource requests by the user applications and, based thereon, generate a map of resource usage by each application; based on the map and the risk database, detect application events associated with risks; and upon detection of an event corresponding to a risk, determining a set of resources vulnerable to the risk and, based thereon, taking an action.

The action may, for example, be issuing an alert to a supervisory node responsible for the determined set of resources or updating a computational system-wide risk model. The system may include an independent sensor associated with each of the user applications or a single sensor responsible for all of the user applications. In some embodiments, the system is a server hosting user applications for multiple endpoint devices and users, and may include an independent sensor associated with each of the user applications. For example, each of the user applications may be hosted for multiple simultaneous user sessions, and the system may include a single sensor responsible for all of the user applications.

In some embodiments, the method further comprises the step of, upon detection of an application event associated with risk, checking the event against a minimum cut set of vulnerabilities stored in a vulnerabilities database.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "approximately" and "substantially" mean±10%, and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

In accordance herewith, risk scores may be generated at a device level by an agent running on the node. A risk score obtained as described herein may be a weighted (and normalized) average of individual risks to confidentiality, integrity and availability, and may be inverted to indicate how well an organization can protect ePHI (in a manner similar to the consumer credit score that measures creditworthiness and the ability for an individual to repay a loan). In this case, the ePHI security score reflects how well an organization can be expected to secure ePHI data based on a comprehensive and automated assessment of internal risks. This approach leverages intelligent agents running on some or all nodes of the system to identify how and what ePHI content passes between an application and system services (e.g., network services or files services), so a dynamic risk model can be utilized and updated to characterize threats and vulnerabilities to security and integrity controls from users, applications and system resources that interact with ePHI.

Figure 1:
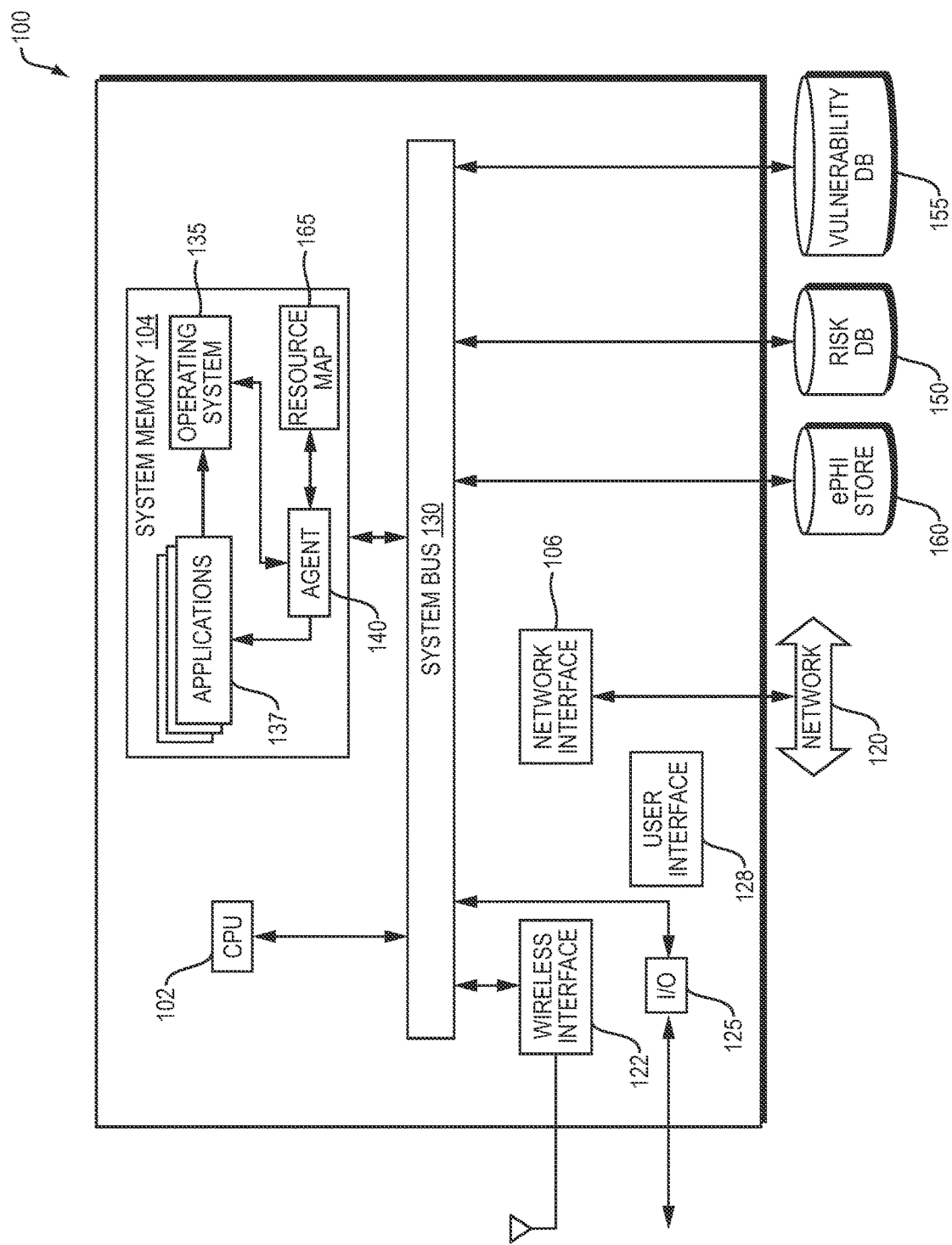
FIG. 1 schematically illustrates a hardware implementation of an endpoint device.

FIG. 1 illustrates a representative endpoint device 100, which typically includes a processor 102 (e.g., a CPU microprocessor) and associated system memory 104, a network interface 106 (for connection to the institutional network 120 and/or the Internet), and, usually, one or more nonvolatile digital storage elements (such as a hard disk, CD, DVD, USB memory key, etc.) and associated drives. A wireless interface 122, which may be separate from or implemented within the network interface 106, facilitates wireless communication with, for example, user mobile devices. The input/output (I/O) block 125 performs functions dictated by the nature of the device 100. A medical monitoring device will have I/O to, for example, physiologic and/or medication sensors with relatively little user access, while an EMR system may include traditional user input/output devices such as a display screen and conventional tactile input devices such as touchscreen, keyboard and mouse or touch pad, etc., and may provide a user interface 128. The various components communicate with each other via one or more bidirectional buses 130.

In use, the processor 102 executes one or more computer programs (conceptually illustrated as program modules) stored in the system memory 104. In particular, an operating system 135 (such as, e.g., MICROSOFT WINDOWS, LINUX, UNIX, iOS, or ANDROID) provides low-level system functions, such as file management, resource allocation, and routing of messages from and to hardware devices (such as I/O device(s) 125) and one or more higher-level user applications (such as EMR applications, office programs, a web browser, etc.) 137. An agent 140, described in greater detail below, executes various functions in accordance with embodiments of the invention. The agent 140 may be implemented by computer-executable instructions, such as program modules, that are executed by a conventional computer. Generally, program modules include routines, programs, objects, components, data structures, etc. that perform particular tasks or implement particular abstract data types. Those skilled in the art will appreciate that the invention may be practiced with various computer system configurations, including multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer-storage media including memory storage devices.

A risk database 150 includes a computational representation of one or more risk models as described below. The risk database 150 maintains a directory of specific risks, their impact, severity, and potential mitigation actions. As the agent 140 identifies vulnerabilities (e.g., privilege escalation), the agent uses the risk database 150 to evaluate the severity of the action (threat) in computing the overall risk and what mitigation actions to take. The risk database 150 therefore becomes the knowledge base for how to respond to different vulnerabilities and threats.

A vulnerability database 155 includes computational representations of represent conditions that, if identified as occurring on the system 100, could be exploited by a threat. The vulnerability and risk databases 150, 155 classify and store vulnerabilities and risk calculation so they can be field updated, e.g., pushed from a cloud server to all the agents so they maintain current awareness of system vulnerabilities, e.g., at the level of the operating system, applications, networks, devices, etc.

Thus, devices as described herein may comprise or consist of a general-purpose computing device in the form of a computer including a processing unit, a system memory, and a system bus that couples various system components including the system memory to the processing unit. Computers typically include a variety of computer-readable media that can form part of the system memory and be read by the processing unit. By way of example, and not limitation, computer readable media may comprise computer storage media and communication media. The system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RANI typically contains data and/or program modules that are immediately accessible to and/or presently being operated on by processing unit. The data or program modules may include an operating system and application programs, as discussed above, as well as other program modules and program data.

Any suitable programming language may be used to implement without undue experimentation the analytical functions described above and in the attached paper. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of the system and method of the invention. Rather, any number of different programming languages may be utilized as is necessary or desirable.

The computing environment may also include other removable/nonremovable, volatile/nonvolatile computer storage media such as solid-state drives, magnetic disk drives, optical drives, etc. Other removable/nonremovable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The storage media are typically connected to the system bus through a removable or nonremovable memory interface.

The CPU 102 that executes commands and instructions may be a general-purpose processor, but may utilize any of a wide variety of other technologies including special-purpose hardware, a microcomputer, mini-computer, mainframe computer, programmed micro-processor, micro-controller, peripheral integrated circuit element, a CSIC (customer-specific integrated circuit), ASIC (application-specific integrated circuit), a logic circuit, a digital signal processor, a programmable logic device such as an FPGA (field-programmable gate array), PLD (programmable logic device), PLA (programmable logic array), smart chip, or any other device or arrangement of devices that is capable of implementing the steps of the processes of the invention.

In some implementations, a device can host one agent 140 that can monitor multiple applications 137 per user session, or an agent can be instantiated for each application instance of a session. On a remotely hosted session (e.g., via CITRIX), the host server runs multiple user sessions and can instantiate one agent 140 that simultaneously monitors multiple applications 137 started by one or more users in different sessions. In a shared environment such as CITRIX, VMWARE or MICROSOFT Remote Terminal Service one agent simultaneously monitors applications 137 launched separately by different users. In a virtualized desktop environment with multiple operating systems running on the same hosting hardware, an agent is associated with each virtual desktop to monitor applications within a user session.

The built-in ability to identify ePHI content means that the agent may locate producers, sources and consumers of ePHI data rather than relying on user reports or ePHI data discovered by personnel (e.g., the information technology department). In various embodiments, confidentiality, integrity and availability have different risk profiles that are represented as paths within an AND-OR decision tree depicting combinations of vulnerabilities in or affecting components that can be exploited to alter security controls governing access control to executable binaries, libraries, data files, ePHI stores, configuration files, registries, network resources, device access and user privileges. This ePHI-centric security model is premised on properly set security controls for ePHI sources, applications, application-dependent components and devices that source or consume ePHI. Dependency-based hierarchical model (which can be explored recursively) in accordance herewith may be generated by automatically identifying sources of ePHI and then narrowing the focus to the immediate ePHI "eco-system" to ensure it is operating within normal operating limits—even within a potentially compromised system. With this approach, as long as the protective eco-system around ePHI is unaffected, the state of the broader system or network is not relevant to the ePHI risk assessment. This assumption obviously would not hold if the operating system itself has been compromised.

The risk model may be represented as a fault tree, as are used to model system failure modes as a combination of AND-OR conditions observed from dependent components. In one embodiment, risk is modeled using a weighted fault tree in which the root is the likelihood of compromise of the confidentiality, integrity, or availability of a specific ePHI store. Internal nodes are AND or OR gates whose children represent the independent necessary subconditions to trigger the parent condition. Leaf nodes are vulnerabilities that can be assigned a numeric weight representing the likelihood of compromise. These weights can then be used to determine the likelihood of triggering a parent conditions as follows:

1. The likelihood score for an AND gate with children whose likelihoods are $L_1, L_2, \ldots, L_n$ is $L_1 \times L_2, \lambda \ldots \lambda L_n$.

2. The likelihood score for an OR gate with children whose likelihoods are $L_1, L_2, \ldots, L_n$ is $1-(1-L_1) \times (1-L_2) \times \ldots \times (1-L_n)$. Continuing in this manner, the likelihood of compromise of an ePHI store can be estimated. Similarly, the most likely means of compromise can be analyzed by finding minimum cut sets in the tree corresponding to the most likely set of leaf vulnerabilities to be exploited. This model can equivalently be adapted to use estimates of the difficulty of compromising leaf vulnerabilities by adjusting the AND and OR gate calculations. Modeling risk using weighted fault trees allows for efficient dynamic updates as new vulnerabilities or changes to a vulnerability's likelihood of exploitation can be incorporated by bubbling up the adjustment through an existing tree. This includes adjusting the risk to incorporate observed exploitations, which are modeled as the likelihood of exploitation going to 1 (or equivalently as the difficulty going to 0). Risk across the system can then be modeled as an aggregation over the individual ePHI stores in a variety of manners to gain different insights into the overall risk profile. As representative but not exhaustive examples, ePHI stores can be weighted by the volume of ePHI contained to understand the likelihood of breaches of different magnitudes. Common dependencies and correlations between different fault trees can also be analyzed to understand system-wide weak points.

Figure 2:
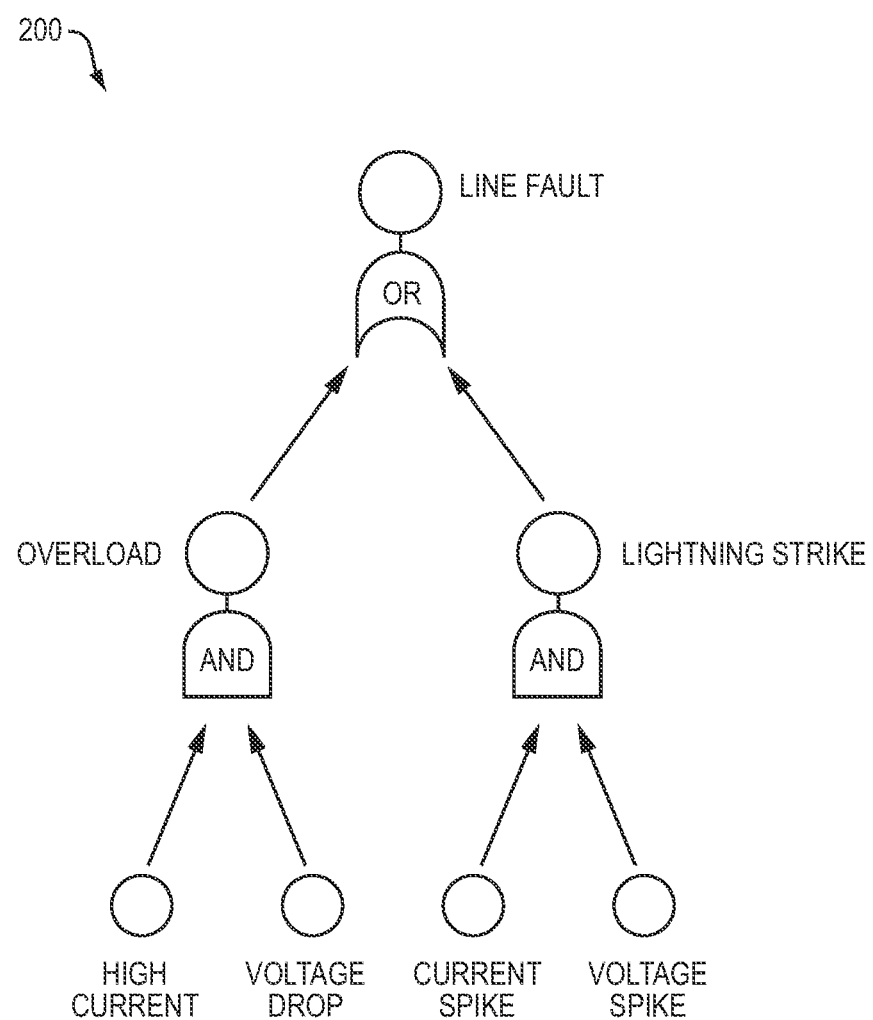
FIG. 2 graphically illustrates a fault tree for monitoring system failure modes.

As a simple example, with reference to FIG. 2, a "line fault" condition in a power system may be due to an overload condition OR a voltage spike condition. The overload condition may be due to measured high current AND a drop in the line voltage while the voltage spike condition is identified as a sustained high voltage (transformer failure) AND low current OR a short-duration spike in current AND voltage (lightning strike). The resulting fault tree 200 for "line fault" characterizes the failure modes based a set of detected conditions. Vulnerabilities may be terminal nodes in a fault-tree. An example of a vulnerability is a software module used by an application that is listed in the CVE (Common Vulnerability and Exposure) database. The vulnerability would be "Known CVE software vulnerability," which would be true in the AND-OR diagram when the version of the module is listed in the CVE database. Another vulnerability can be, "Module is different from previous inventory version"—this would be true if a new version of a library that was not used before is now being loaded and used. These and other vulnerability conditions are stored in the vulnerability database 155 and in evaluating risk.

In various embodiments, the risk to ePHI is represented as a failure mode caused by the exploitation or compromise of a set of vulnerabilities found in application components (e.g., a software library) or security controls used to control access to ePHI data or application components. Threat conditions (e.g., a privilege elevation or active attack by malware loaded on the same machine with the privileges to bypass process-execution boundaries set up by the operating system) that compromise a set of identified vulnerabilities would ultimately affect the ability of the system to ensure confidentiality, integrity or availability of ePHI. The risk fault tree, then, may be AND-OR combinations of component vulnerabilities that model how observed conditions (threats) can lead to a compromise of components and ultimately affect individually or separately confidentiality, integrity or availability of ePHI in, for example, an ePHI store 160.

The agent 140, by running as an embedded thread of each monitored application 137 (within the same address space), has visibility to the set of statically and dynamically loaded library modules as well as all system resources (including input and output to connected devices) that the application 137 uses. The agent 140, in real-time, keeps track of the files that are opened, the privileges asserted, the registry keys and configuration files accessed, attached devices used and network services requested. As application requests are made for each resource, the agent 140 dynamically builds an application resource map 165—e.g., a tree data structure storing identifiers of the dependent system components, and adds more nodes to the tree as the application continues to run and request additional resources. To monitor resource requests, the agent may intercept API calls in the manner described in U.S. Ser. No. 16/286,962, entitled "Resilient Management of Resource Utilization" and filed on Feb. 27, 2019 (the entire disclosure of which is hereby incorporated by reference).

The parent-child relationship that exists between the components together with the security controls that govern read/write access to these resources lay out a map that a potential rogue software program or a malicious user could use to attack the execution of the application or even directly interact with critical ePHI data. Changing the values of a shared configuration file used by an application, for example, can result in loss of application integrity or availability because the dependent component was not adequately secured. The application resource map 165 provides a blueprint of the dependent resources used, the security controls that protect their access and the mechanisms (vulnerabilities) that can be exploited to compromise either the application or the ePHI store. That is, the resource map 165 is what the agent 140 analyzes to identify how to reinforce or nullify potential vulnerabilities as well as to establish risk to the ePHI source.

The agent 140 can be deployed in various ways depending on design preferences. As noted above, a single agent 140 may monitor multiple applications 137 per user session, a separate agent 140 may be instantiated for each application instance logged, or a dedicated agent may be deployed just to monitor a particular application. Alternatively, the agent 140 may be deployed on a hosted environment rather than on every endpoint device and accessed by the various devices via the network 120. For example, with hosted applications running on a server supporting multiple user sessions, one agent 140 may simultaneously monitor multiple applications 137 started by a particular user. In various embodiments, the agent creates an application resource map 160 of all the resources used by each application 137 that it monitors. The application resource map 165 serves as an inventory of all resources, including system resources and devices, that a program uses when it is initially loaded into memory and when it is running. System resources in this context refers broadly to any physical or logical capability managed by the operating system 135 because either it is a shared commodity (e.g., the CPU, memory, disk, etc.) or it is under access control because the information or functionality has value and therefore the potential for misuse (e.g., a database, application server, network port, system configurations, WINDOWS registry). This is information that application vendors may or may not provide, and which in any case is constantly changing; a static map is not useful.

Characterizing what resources an application 137 uses and how it uses them provides an effective approach to determining whether the application can have a detrimental effect on the device 100. The more requests for resources that an application 137 makes, the greater the risk it represents; this applies to trusted enterprise applications as well as newly installed applications; even trusted software can be hijacked by malware at runtime to evade antivirus detection, for example. The system described below performs real-time examination and control of the resources used by an application 137 to dynamically determine whether these are legitimate uses and whether the resource should be used by the application. In effect, this system may represent the last line of defense for the device 100 as it superimposes a run-time behavioral sanity check on resource use. This defensive approach to protecting system resources may trigger responses such as access blocking if there is doubt as to legitimacy of the application 137.

Figure 3:
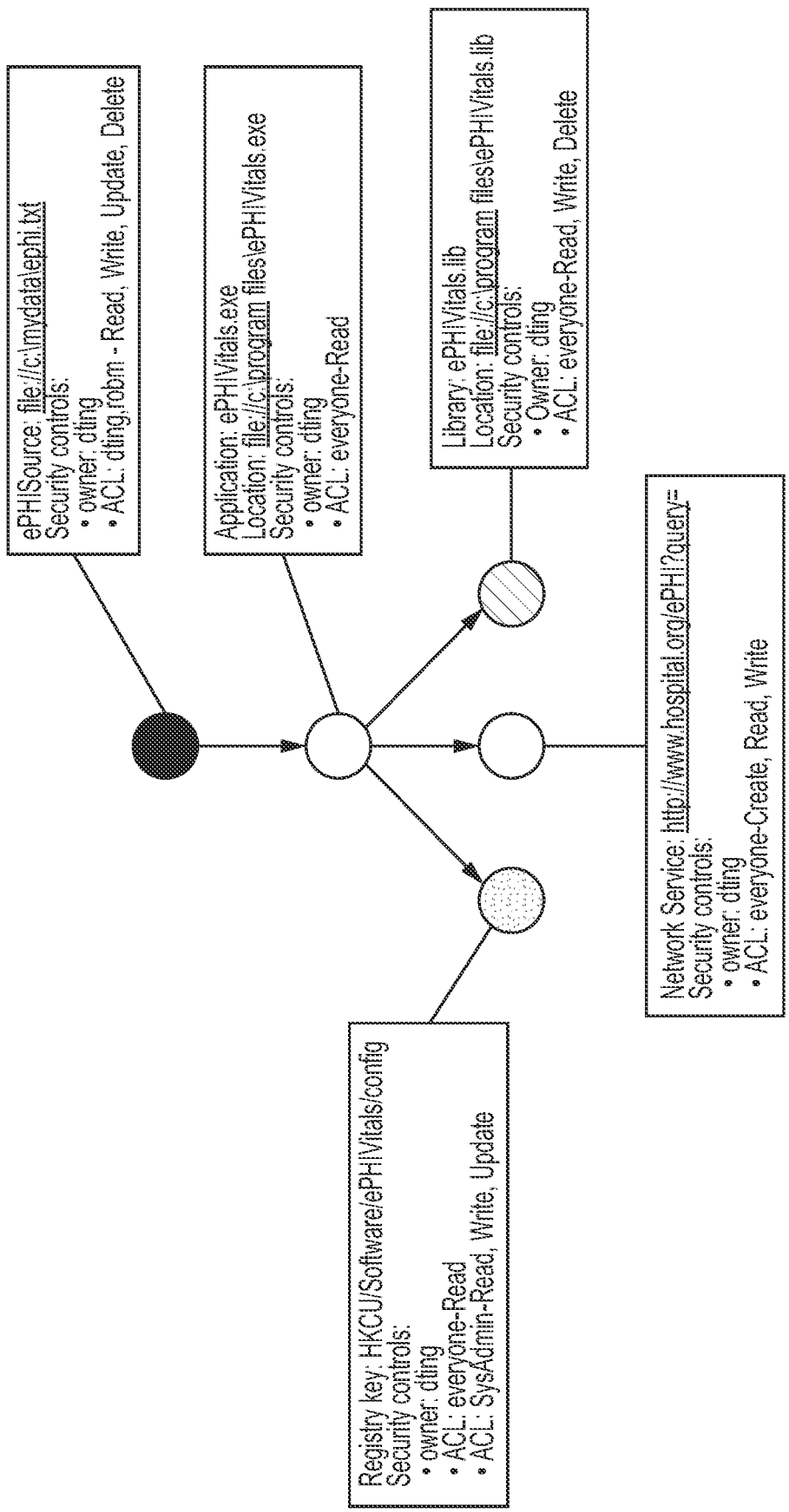
FIG. 3 graphically illustrates a resource map for a representative application.

Consider an application that reads and writes ePHI from a local file. The resource map for the application might conform to FIG. 3, in which the ePHI source file://c:/mydata/ePHI.txt is accessed by application instance ePHIVitals.exe from a stored binary file://c:/program flies/ePHIVitals.exe. The application accesses configuration data in the registry stored locally in HKCU/software/ePHIVitals/config and at runtime loads library functions from ePHIVitals.lib, which is located at file://c:/program_files/ePHIVitals.lib. The program also access http network services to connect with an in-house server, http://www hospital.org/ephi. This information, together with the security control settings for the ePHI.txt file, can then be used to build the risk model.

In fault tree analysis (FTA), a "minimum cut set" is the smallest set of individual component faults required to trigger a root-level fault. With continuous risk analysis, this corresponds to the minimum number of vulnerabilities that, if exploited (by threats), would compromise CIA of a specific ePHI source. The agent 140 associates with each dependent component potential vulnerabilities that, if exploited, would affect CIA of the associated top-level ePHI store 160. In various embodiments, the role of the agent 140 is to discover these dependencies, and the vulnerabilities associated with each resource are defined for the agent 140 by, for example, the risk database 150. The risk database 150 may reflect vulnerabilities that have been discovered (as in the CVE database, described below) or entered (or overwritten) by a user with administrative privileges.

Different tree data structures 165 may be used for confidentiality, integrity and availability to characterize vulnerabilities that exists for each resource type. It should be noted that resources can be compromised by a program if security controls are not properly set or can be overwritten by another program/user with administrative privileges to gain Read, Write, Update or Delete access. The user with administrator privileges, therefore, presents the ultimate threat by being able to bypass all security controls.

Risk to Confidentiality

Risk to confidentiality occurs when the contents of an ePHI store is accessed (or has the potential to be accessed) by an unauthorized user or program. Confidentiality involves maintaining the privacy of the ePHI at rest, in transit and in use. An entire class of vulnerabilities that affect confidentiality can be attributed to users who can gain unauthorized access to ePHI due to inadequate user authentication to ensure proper user identity. Improperly set security controls for an ePHI store, for example, may allow another program or user to gain Read access to ePHI data if the Read access is set to "anyone." Alternatively, a user who has not been adequately or strongly authenticated (or authorized) may gain access either through the system (attacking the data) or through an application like the electronic medical record (EMR) manager. Confidentiality can also be breached during session switching, e.g., if a second user forces the existing user's session to terminate while the patient records of the existing user are still displayed.

Technical vulnerabilities for confidentiality can involve lack of encryption when ePHI is written to files, data is sent across the network in plaintext (e.g., http) as opposed to secure cipher text (e.g., https), or copied to removable media (e.g., a USB token) or archived storage (as opposed to a secure, encrypted file system). ePHI can also be exposed in the cut-and-paste buffer, cached browser or desktop, or spooled printer files when shared workstations are use. The contents of the clipboard buffer (used for cut and paste) may not be cleared during user transitions and, in systems hosting a shared desktop, can expose data from a patient record retrieved by the previous user. These vulnerabilities are linked to resources used by ePHI applications and identified by the agent intercepting API calls. The risk model for each type of resource (e.g., file) identifies whether ePHI is being exchanged (over the system call) and what privacy controls are in effect. If ePHI is being sent over the network, for example, the risk model identifies a vulnerability if TLS/SSL/FTPS is not being used as the channel can be compromised by a man-in-the-middle attack or sending data to a spoofed server. A similar vulnerability is identified if a file read/write with ePHI data is performed against an unencrypted file system or ePHI data is left in a clipboard buffer, html cache or a printer spooler when a user session ends. Additional vulnerabilities may arise when data is copied to removable media (especially in unencrypted format), as it is not possible to track where the data may end up.

Vulnerabilities for displayed ePHI are more difficult to model except for the case when an ePHI application is in foreground mode (presumably with ePHI displayed) and the session is forced to terminate by a second user. The vulnerability for "ePHI left on display" corresponds to a threat where an ePHI application in active foreground mode is forced to terminate the session so a second user can gain access. An ePHI application left in active foreground mode but idle (no user activity) for a long time presents a similar vulnerability.

The risk model for confidentiality is developed dynamically from system resources that the application requests and the manner in which privacy is (or is not) protected—typically with encryption or appropriate use of screen locks. ePHI confidentiality is also affected by consistency in the manner in which it is accessed and whether there is similarity in the set of users, applications and usage patterns at a given time compared to historical averages or patterns. Similarity in usage patterns is strongly user-dependent, as clinicians have different roles and workflows and access different ePHI. A clinician who normally accesses ePHI from a clinical setting, for example, would not normally be accessing financial applications used by the business office. The utility of similarity measures for risk modeling lies in identifying vulnerabilities such as copying ePHI data to removable media or sending ePHI data to external sites—usage patterns that represent a departure from prior practice. This approach will identify, for example, a rogue application that starts exfiltrating data over the network to an unknown URL.

Risk to Integrity

Risk to integrity occurs when the contents of an ePHI store are (or can be) altered in an untraceable fashion (i.e., tampered with) or if the integrity of an application capable of accessing it cannot be verified. Integrity of access relies on properly authenticating users to ensure the identity of the user making changes to ePHI. It should be understood that ePHI applications are not only those that clinicians use to create, store, transmit or receive ePHI, but also include medical devices or "Internet of things" (IoT) devices that generate or consume ePHI (e.g., an infusion pump or cyberknife surgical device). Vulnerabilities that affect integrity can be attributed to improperly set security controls so that another process (or user) can tamper (write, update) or compromise (delete) ePHI or applications that interact with it. In the above example, ePHI integrity is at risk because security controls for ePHIVitals.lib used by the ePHIVitals app accord everyone Write and Delete permissions (instead of just Read access). This allows someone to modify or replace the real ePHIVitals.lib with a fake one (or a wrapped one) and compromise how ePHIVitals.exe interacts with ePHI. Configuration data, however, is properly secured in the registry key, as it accords everyone Read only access and Read, Write, Update access only to the system administrator. Threats to the vulnerabilities identified in the system vary in technical complexity and implementation difficulty. Some vulnerabilities, such as hijacking an application, require the malware to embody an understanding of the structure of the application, to be installed on the target machine where the application is running, and to have administrator rights. The degree of difficulty in exploiting a vulnerability can be used in weighting the risk associated with the vulnerability. This data can be maintained in the vulnerability database 155.

The vulnerability common to all components is the user with elevated administrator privileges that can override, within his session, the access-control settings used to safeguard improper access or overriding the access controls in place to safeguard a resource. Processes inherit privileges from the logon session created by the authenticated user, so every resource is vulnerable depending on the initial privilege level associated with the application. Privileges for an application can also be elevated by a user impersonating a user with a higher level of privilege. The risk level obviously goes up if the logon session associated with the application either has elevated privileges or the ability to elevate privileges (using administrator credentials or a token from a system-level process).

ePHI application integrity can be compromised if malware running within the same session is able to overwrite parts of its program (i.e., change executable program memory), either to hijack it or surveil its operation. This vulnerability is present if malware succeeds in running with elevated privileges to inject malware code or open the process memory and rewrite executable memory ("rewiring" the application). The risk to ePHI integrity from external applications (running within the same session) is represented in the risk model as a vulnerability to code modification by a peer process (i.e., a non-child process). In a WINDOWS environment this means malware must use high-risk system calls (such as OpenProcess or WriteMemory for WINDOWS applications) against a running application. Use of these calls is monitored by the agent 140 as it has visibility to API use within all processes running on the endpoint, and can detect when another process is attempting to gain access to a legitimate process accessing ePHI.

Malware can also parasitically inject rogue code as a thread into a running application and achieve similar results. In this case, the CreateRemoteThread function (part of the MICROSOFT WINDOWS SDK) is used to associate a thread with a running process to either surveil or hijack the process. Other methods may involve "hooking" the program to cause the operating system to load malicious code into a target program without the program detecting it. These approaches are often used to cloak malware inside a running, trusted application to avoid detection. Again, the agent 140 running on all processes can detect when another process is attempting to graft software onto a running process.

Application integrity can be compromised if a module used by the application has a known vulnerability and is in the public Common Vulnerabilities and Exposures (CVE) database available at https://cve.mitre.org/. This a priori knowledge is accounted for in the risk model, as it increases the likelihood the application is or can be compromised regardless whether a threat is present. If the characteristic of the vulnerability is well established and can be associated with specific runtime conditions (e.g., use of SMB for lateral migration) or API calls, then the risk model can be further refined with additional AND-OR conditions for improving threat detection. Absent this level of detail, it is sufficient in most cases to model the risk potential generically, e.g., as "dependent module has known vulnerability."

Each ePHI store or dependent application component has a set of vulnerabilities depending on the resources used. As the agent (or agents) 140 intercepts API calls from all processes (including applications 137) within each endpoint device or server 100, it checks these against the minimum cut set of vulnerabilities stored in the vulnerabilities database 155 to see if the API call or external conditions (representing threats) are sufficient to potentially compromise ePHI integrity. Normally the agent within or responsible for each process monitors the API behavior for itself and child processes, but if it detects attempts to access processes or associated resources that belong to a peer process, it can alert the agent on the target process so the alerted agent can determine whether there is a threat to its program integrity.

ePHI integrity is also affected by consistency of use and whether there is similarity in the current set of users, applications and usage patterns against patterns discovered over time. Similarity in usage patterns is strongly user-dependent, as clinicians have different roles and workflows. Its use in risk modeling is to identify vulnerabilities such as access of ePHI by new applications (e.g., WINDOWS Explorer or a browser), access by unknown applications and access by unknown users or users with different privilege levels.

Risk to Availability

Risk to availability occurs when applications that handle ePHI for a user are unable to deliver a satisfactory level of service. Unsatisfactory service levels can range from complete inability to access a computer (due to, e.g., ransomware or DOS attack), failure within a logon session to launch an ePHI application (due to, e.g., network or server connectivity issues), performance slowdown (e.g., database requests taking too long) within an ePHI application caused by a resource constraint, to inability to access attached devices (e.g., printer not working). Vulnerabilities that affect risk to availability are tied to the latency associated with servicing requests made by an application. The risk model can be rooted to an ePHI store or an ePHI application for the purpose of establishing risk, since they are similar.

The availability risk model is developed from the expected (e.g., average historical) latency measured from resource calls made by each application. This statistical model can be used to determine the expected performance bounds for an application from the perspective of typical resource use calls, and if necessary, may include additional components such as number of endpoint devices, amount of endpoint volatile memory, endpoint storage, network-to-server connection speed, server name, server type, server memory, amount and type of ePHI data, etc. to correlate additional data points for the statistical model.

Risk to availability may also be influenced by non-ePHI applications (e.g., crypto jacking or ransomware), which may affect the ability of the ePHI application to run properly. The risk model for availability has additional nodes that represent conditions generated by agents in non-ePHI applications when they encounter anomalous situations such as an unknown process running on one or more endpoints (not used throughout the organization); a process sourced from the internet that is opening many files (e.g., ransomware); a new process consuming large amounts of CPU time (e.g., crypto miner); a process attempting or using privileged API calls (e.g., OpenProcess or AdjustTokenPrivileges), opening ports to external URLs or attempting to connect to internal server ports. When an agent 140 (bound to a process such as an application 137) identifies these types of suspicious behavior, the information is made available as input to the risk model used by other processes. Similarly, alerts produced by technical security products such as ANTIVIRUS (AV) or Endpoint Detect and Respond (EDR) processes can be included to augment the risk model as well.

ePHI availability is affected by consistency and similarity in actual latency measured for resource against historical latency collected over time. Similarity in application resource use is dependent on users, endpoint devices, time of day, day of the week or month, and backend server connection and load. In the approach described above, the agent 140 maps resource usage and detects specific events. Those events, and the risks associated with them, reflect resource-specific vulnerabilities and are dictated by the risk model, which may be in database form. The resources, vulnerabilities and risks differ for confidentiality, integrity, availability. For the simple system shown above, representative risks to confidentiality and approaches to handling them are set forth in the below table.

TABLE 1

| | | Risks to Confidentiality | | |
|---|---|---|---|---|
| Resource | Vulnerabilities | Agent detects . . . | Risk | Minimum cut set |
| Network service | Inadequate server authentication Un-encrypted channel | Type of network protocol used and if server identify is used Type of network protocol used - SSL or non SSL | Loss of data privacy from sending data to unknown server Loss of data privacy from potential packet sniffing | external IP network port opened non-SSL connection is used server identity is not verified ePHI is detected in data stream network connection is opened (local or remote) non-SSL connection is used ePHI is detected in data stream |
| | Exfiltration of ePHI | Network transfer of ePHI to external IP address | Deviation from institutional average; deviation from user average | network connection is opened ePHI data is sent out IP address or ePHI data stores used are not typical process accessing ePHI does not have UI, is newly installed or not typically behavior for user |
| Local or network file | Improperly set security controls | Access permissions requested when app opens the file | Improper access by others users | file is opened access permissions are not exclusive to app user ePHI is detected in data stream |
| | Un-encrypted storage of persisted data | Type of file system being used | Improper access if the file is lost or stolen | file is opened file contents are un-encrypted ePHI is detected in data stream |
| | Removable storage media | Type of storage device used | Data exfiltration | removable storage media opened ePHI file or content is written to device removable media use is not typical for user removable media is ejected within user session |
| Registry key | Improperly set security controls | Access permissions requested when app opens the key | Improper access by others | key is opened access permissions are not exclusive to app user ePHI is detected in key content |
| Application Library | Application hijacking by malware | Attempts by a different process to inject code into application | Data surveillance or exfiltration | external process elevates privilege external process overwrites application executable memory or injects thread application (with injected code) opens files or server connections and exchanges ePHI |
| Display | ePHI exposure on shared workstation | User authentication to shared workstation and state of application | User is exposed to ePHI left by application left running by first user | ePHI application started by first user is visible second user preempts the first user's session on the shared desktop |

Figure 4A:
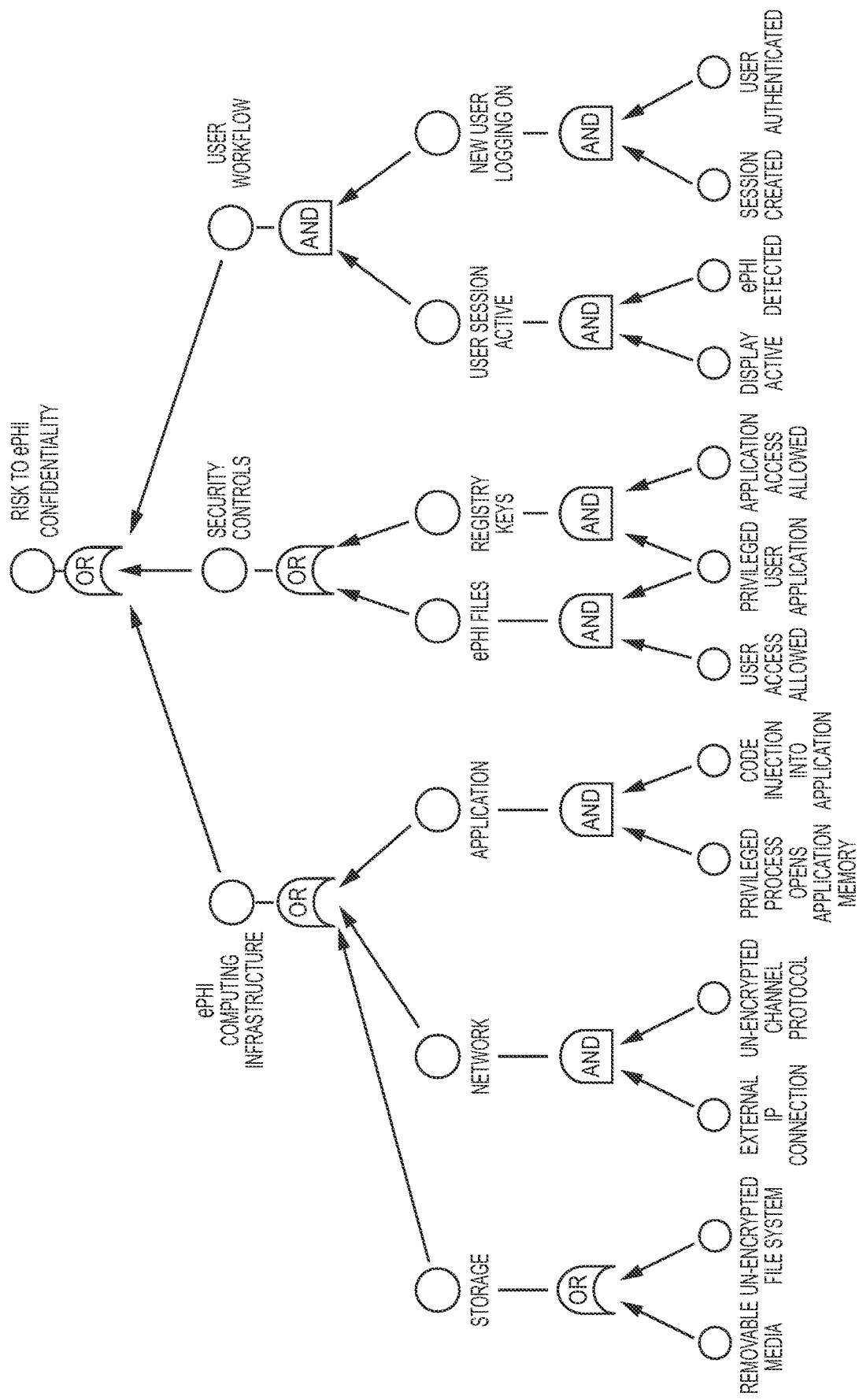
FIG. 4A graphically illustrates a model for risks to confidentiality.

An AND-OR risk model for confidentiality is shown in FIG. 4A, where the first level of OR states is triggered by different vulnerabilities from the ePHI computing infrastructure, security controls and user workflows. An AND-OR risk model for confidentiality is shown in FIG. 4B.

Figure 4B:
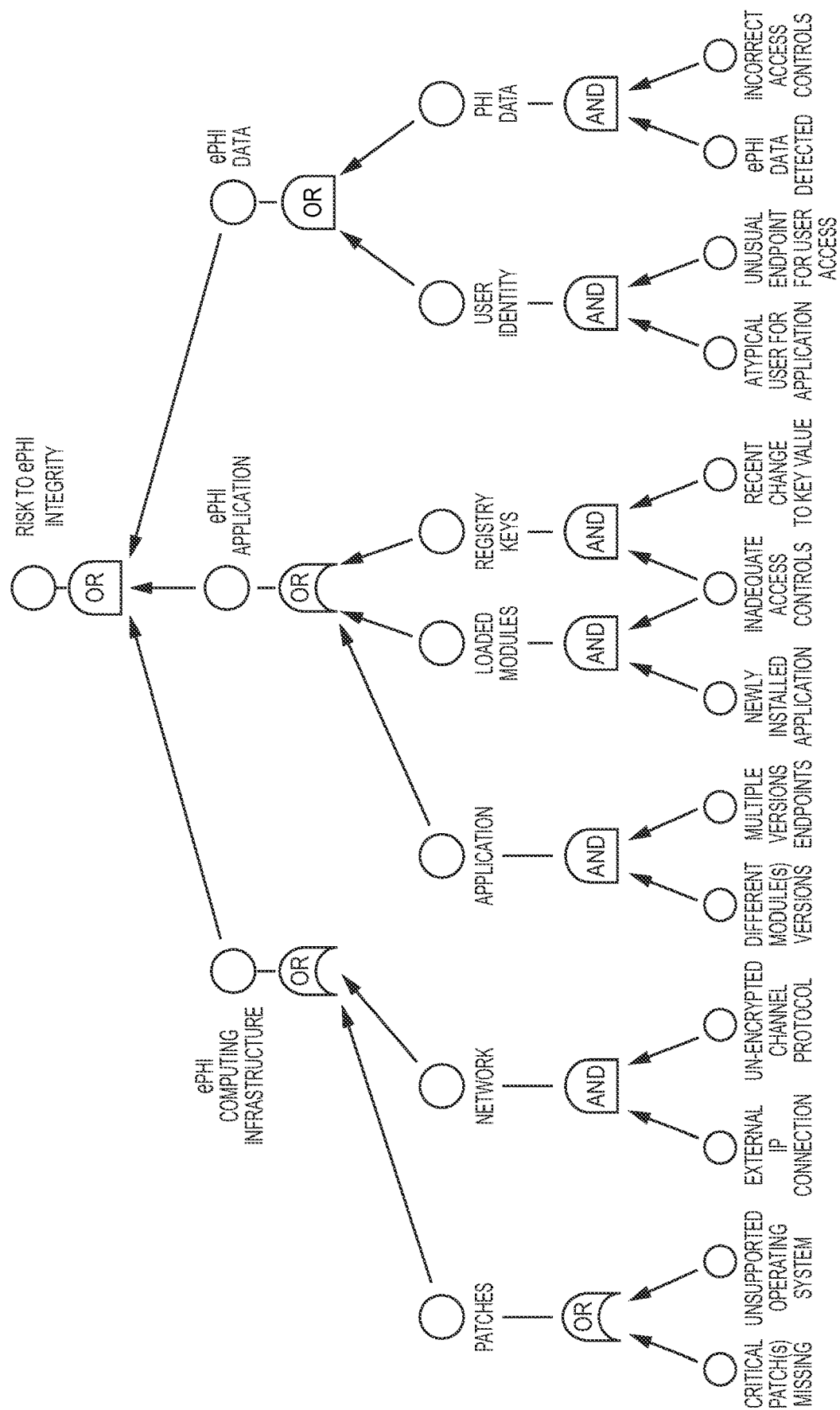
FIG. 4B graphically illustrates a model for risks to integrity.

The risk models shown in FIGS. 4A and 4B may be readily represented as a graph (e.g., tree) data structure and stored in the risk database 150. Each type of risk (e.g., Storage) has a specific set of dependent conditions that, if present, would potentially compromise C, I or A. Storage risk for ePHI will be present, for example, if removable media and unencrypted storage is used for storing PHI. The minimum cut set is determined by traversing the AND-OR graph data structure to find the shortest path that would lead to a root-level risk. Risk to ePHI, for example, can come from a compromise of either the computing environment, the security controls or user workflow. The minimum cut set is the path with the easiest set of conditions—in FIG. 4A, this would be from the use of an unencrypted file system on a removable medium. Minimum cut sets allow the robustness of the system to vulnerabilities to be understood. The longer a minimum cut set is, the more robust it is to threats as more combinations of events must simultaneously occur. A large number of cut sets is similarly an indicator of susceptibility to threats, as there are now more ways to compromise the system. For each cut set (i.e., path through the tree), a probability can be assigned to further model the likelihood of occurrence of the events that can trigger a fault condition.

The fault tree associates AND-OR vulnerability conditions stored in the vulnerability database. The storage organization of vulnerabilities, their dependencies (AND-OR connectors) and conditions (e.g., removable media, unencrypted storage, everyone access, etc.) can be implemented using any suitable data representation format, including but not limited to SQL tables, JSON name-value collections, and Google Protobuf.

Representative risks to integrity are set forth in the below table.

TABLE 2

Risks to Integrity

| Resource | Vulnerabilities | Agent detects . . . | Risk model | Minimum cut set |
| --- | --- | --- | --- | --- |
| Network service | User downloads and installs malware code | Download of data from external IP address | Deviation from behavior norm for user | browser opens network connection to remote site browser downloads and stores data on file system browser initiates execution of either script engine or binary executable as child process |
| | Advanced Persisted Threats (APT) | Processes without UI accessing local and remote network resources | Deviation from institution norm for the system or the user | running process has unknown origin or newly downloaded process doesn't present UI and auto starts or persists across sessions process opens remote network connections process requests or consumes resources |
| | Unauthenticated access to ePHI | Non-use of TLS/SSL/FTPS | Application is connecting to an unverified server | external IP network port is opened non-SSL connection is used server identity cannot be verified ePHI is detected in data stream |
| Registry key | Unauthorized configuration change | Registry key is opened for write, update or delete | Deviation from institutional norm | external process obtains or has elevated privilege external process opens registry key external process modifies configuration data |
| Library | Application hijacking by malware | Attempts by a different process to inject code into application | Hijack or compromise of application code | external process obtains or has elevates privilege external process overwrites application executable memory or injects thread application (with injected code) opens files or server connections and exchanges ePHI |

TABLE 2-continued

Risks to Integrity

| Resource | Vulnerabilities | Agent detects . . . | Risk model | Minimum cut set |
|---|---|---|---|---|
| | Modifying application behavior | Change to a library file used by an application | Deviation from institutional norm | library file(s) for an application is over written by a new file<br>library file(s) are not on approved list<br>new library file(s) make resource use that are different than before<br>new library file(s) use API calls considered risky |

Representative risks to availability are set forth in the below table.

TABLE 3

Risks to Availability

| Resource | Vulnerabilities | Agent detects . . . | Risk Model | Minimum cut set |
|---|---|---|---|---|
| Network service | Ransomware, DOS attack, Server or network issues | Latency for network server requests | Deviation from historical or institutional average; deviation from user average | network port is opened against server or peer request service time (latency and throughput) greater than norm |
| Computing | Lack of system resources | Unable to start ePHI application | Deviation from institutional average for access to resources for startup | user session has proper access rights<br>error starting application as child process<br>latency to application ready to accept user input greater than norm |
| | Application slowdown | Latency associated with servicing resource requests | Deviation from institutional average for runtime behavior | latency for servicing one or more resources greater than norm<br>error occurs while servicing request |
| Attached devices | Inability for application to connect to device | Error associated with opening a named device | System configuration deviates from norm | application attempts to connect to device resource is missing or not accessible |
| Malware application | Cryptojacking, ransomware | Newly downloaded process(es) running on endpoint | Deviation from institution norm for allowed application | executable is from newly downloaded file<br>application runs in the background or does not present a UI<br>application makes risk API requests<br>application consuming resources |

Continuous Risk Score

Each risk model defines a set of conditions which, if some subset (i.e., the minimum cut set) is met, would result in an actionable risk level (e.g., a high likelihood that one or more system resources have been compromised leading to the likelihood of an ePHI incident). If the necessary conditions are not met, however, there still exists some level of risk (or potential risk), with the risk level elevating as more conditions are met. In a continuous risk-assessment approach, as the agent 140 monitors an application's resource use, it constantly compares detected uses against conditions in the vulnerability database 155 to determine if they match those associated with a minimum cut set representing some type of risk. A file copy operation (for example, one that reads ePHI data from an encrypted file and moves it to an unencrypted file stored on a removable medium) would satisfy the minimum cut set described above for a confidentiality risk.

Each identified ePHI store has an associated vector of CIA risk, each with its own normalization weight to determine the contribution for confidentiality, integrity and availability to an aggregate risk score. Since providers may have millions of patient records, the aggregate risk score across all ePHI stores is a macro-indicator of how well ePHI records are being secured across all nodes, applications, users and time. Selective scores can be used to narrow down the set of ePHI used (such as those from just the EMR) by applications (e.g., lab or imaging) and by users (clinical, research) to within specific time windows, nodes, I/O devices or specific extranet locations. Constraining the factors used to compute the score allows an IT organization to address specific risks associated different operational workflows (e.g., security risk for ePHI leaving the organization or risk for researchers working with ePHI on their laptops).

The weighting for an individual ePHI risk score can be further refined to account for workflow considerations such as the number of applications that interact with it, the number of users using it including the number of transactions performed against it, the size of ePHI data, whether it is received to/from an internal or external IP address, when the ePHI was created and even if the ePHI was the result of a cut and paste exchange.

In general, the present approach assesses risk based on the number and type of resources that can potentially be compromised (with an ePHI store being far more significant than a local file, for example) by the number and type of vulnerabilities present on a node. Depending on the vulnerabilities and threats present, an agent might report different risks for ePHI being accessed at a given time on a particular node. The higher the risk score is for an ePHI store or source, the more probable it will be that the threats can lead to exploitation of the vulnerabilities. The maximum of all the risk scores on a node at a given time is an indicator of compromise likelihood, and when examined across all nodes (at a given time), the distribution of the scores is indicative of how well the system is securing ePHI. A flat distribution with no high scores is the best outcome. A distribution with several spikes with high risk scores indicates a problem.

In addition, the number of patient lives accessed within each ePHI store can be similarly used to estimate the expected impact of a compromise, assuming there are no boundaries to limit the extent of ePHI damage. That is, while it is possible to treat risk as being defined purely by the infrastructure (e.g., applications, security controls, etc.), the impact in a clinical setting should also account for the way the ePHI impacts patient lives. The ability of the agent to pull patient identifiers from the ePHI data can be used to facilitate tracking the number of patient lives handled by an application and/or a data store; this figure suggests the potential impact of a compromise. Should a config file for the EPIC medical records system be compromised, for example, the impact will be broad because it can affect clinical access to all patient records.

Risk values generated by the risk models indicate the number of vulnerabilities and threats identified in the system at a point in time based on what agents 140 discover while monitoring activity across the nodes 100. A single aggregate risk score obtained from the risk distribution across all nodes 100 (and normalized) can hide the significance of a single node that may be potentially at risk—e.g., a user copying large amounts of ePHI to an unencrypted removable media, because this high-risk activity would be averaged out by all the nodes with low risk. Nonlinear filtering can be used to mask the influence of nodes with risk scores that are near normal within a time window so as to increase the weighting for those nodes that are above normal. A median window filter, for example, can be used to find the median risk score across risk samples taken over several minutes across all nodes (or selected groups of nodes) to further enhance the contribution of individual node risk scores to the aggregate risk distribution.

The aggregated risk score represents the possibility of compromise to CIA with both the shape and scale of the risk distribution serving as predictors for how readily compromise may occur. An indicator of how well an organization is doing to protect ePHI (the security score) can be similarly computed from the shape of the risk distribution and knowledge of the number of nodes that have high risk scores (i.e., the area under the curve). A flat distribution across all nodes handing ePHI with no individual risk scores above a certain number indicates that the system is performing well to ensure ePHI CIA. A distribution with a large cluster of nodes showing high risk scores, by contrast, indicates a system doing a poor job. An ePHI security rating score can be as simple as a measure of the percentage of nodes with risk scores below a threshold to show, for example, that ePHI would be secured at 95% of the nodes but a 5% chance exists that the ePHI could be on a less-than-secure machine. The magnitude of the risk may be considered in the calculation so that a small number of high-risk nodes will lower the contribution from a larger number of low-risk nodes and amplify the reported potential for compromise.

Figure 5:
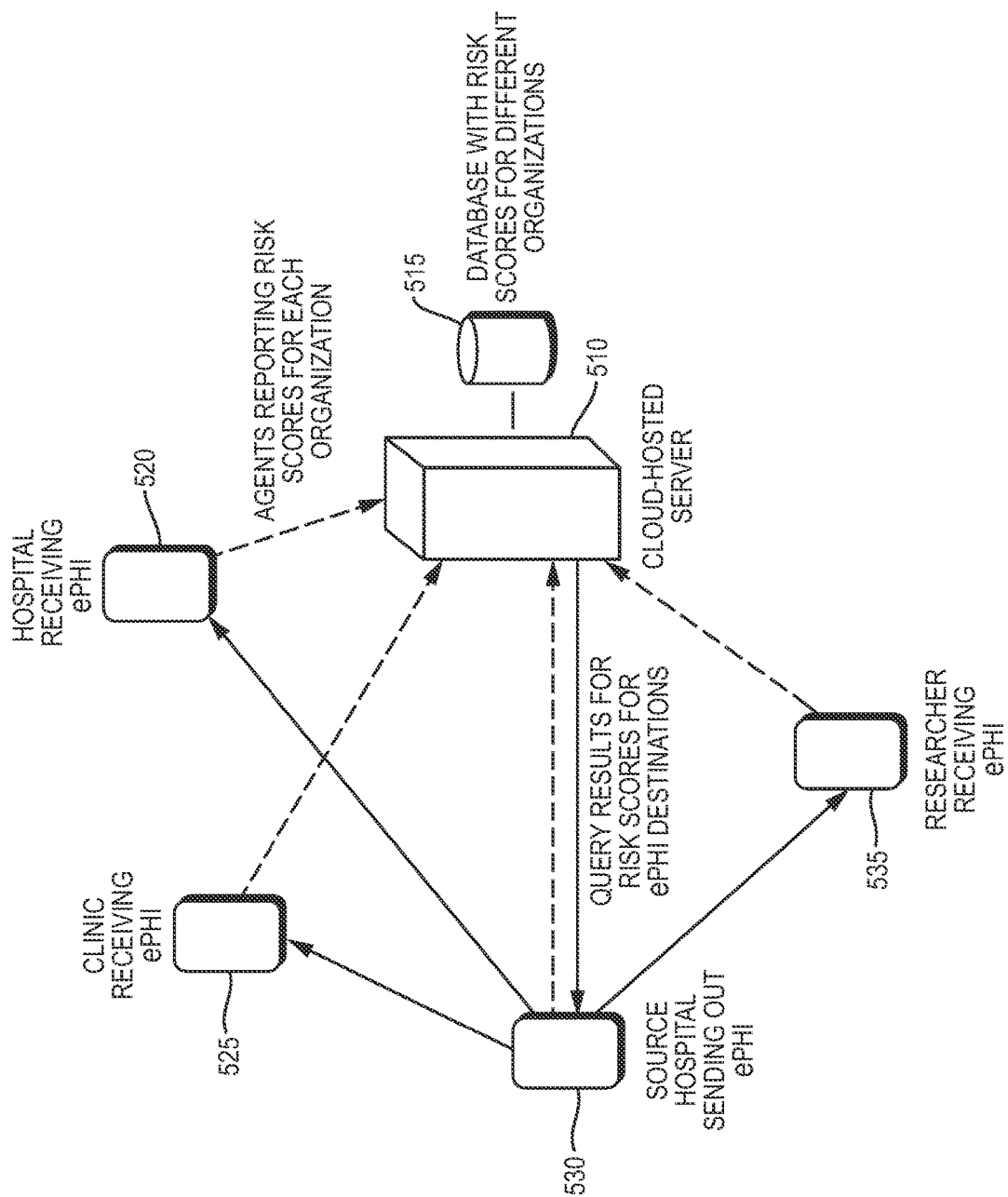
FIG. 5 schematically illustrates a cloud-based system for maintaining and propagating risk scores at an institutional level.

With reference to FIG. 5, a cloud-hosted server 510 may maintain a database 515 of the security rating scores (or the distribution of the risk scores) for different healthcare organizations 520, 525, 530, and individuals 535 who send and receive ePHI. When one of these entities (or individuals) assumes the role of sender, that entity 530 may query the database 515 via the server 520 to obtain a risk score for the proposed destination outside its care-delivery network. The database 515 can retrieve a security rating score for the destination by IP address, hostname or organization name. The query results returned to the sender 530 enables it to determine whether the proposed destination has a risk score commensurate with the sending institution's security policy. The cloud-hosted server 510 continuously receives security ratings (either as a distribution or a security rating score) from agents at institutions and associated with individuals in the network, and organizes the results into the database 515 with security scores for different organizations and individuals (indexed by IP address, hostname(s) or organization names). The security rating scores may be made available through the cloud-based server 510 either as a Web API server for server-to-server connections or as a direct-facing web browser enabling subscribers to look up the scores for different organizations and individuals. A hospital interested in sending ePHI data to a receiving clinic, for example, would obtain and use the security rating score for the clinic to determine if the hospital's guidelines for ePHI security are met before electronically delivering the information. Since each organization is continuously sending updated rating scores, the cloud-hosted server 510 and database 515 may maintain instantaneous and time-averaged rating scores for all participating institutions and individuals.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A computational system comprising:
   a. a processor;
   b. an operating system;
   c. a computer memory;
   d. a plurality of user applications;
   e. a risk database; and
   f. at least one agent executable by the processor and configured to (i) monitor resource requests by the user applications and, based thereon, generate a map of resource usage by each application; (ii) based on the map and the risk database, detect application events associated with risks; and (iii) upon detection of an event corresponding to a risk, check the event against a minimum cut set of vulnerabilities, wherein the minimum cut set of vulnerabilities is the smallest set of individual component faults required to trigger a root-level fault, determine a set of resources vulnerable to the risk and, based thereon, take an action, wherein a resource is a physical or logical capability managed by the operating system.

2. The system of claim 1, wherein the action is issuing an alert to a supervisory node responsible for the determined set of resources.

3. The system of claim 1, wherein the action is updating a computational system-wide risk model.

4. The system of claim 1, wherein the system is an endpoint device.

5. The system of claim 4, wherein the system includes an independent sensor associated with each of the user applications.

6. The system of claim 4, wherein the system includes a single sensor responsible for all of the user applications.

7. The system of claim 1, wherein the system is a server hosting user application for multiple endpoint devices and users.

8. The system of claim 7, wherein the system includes an independent sensor associated with each of the user applications.

9. The system of claim 8, wherein each of the user applications is hosted for multiple simultaneous user sessions.

10. The system of claim 7, wherein the system includes a single sensor responsible for all of the user applications.

11. The system of claim 1, wherein the map identifies dependent system resources requested by the applications and security controls that govern read/write access to such dependent system resources.

12. A method of detecting and responding to computational risks in a computational system comprising a processor, an operating system, a computer memory, and a plurality of user applications, the method comprising:
monitoring resource requests by the user applications and, based thereon, generate a map of resource usage by each application;
based on the map and a risk database, detect application events associated with risks; and
upon detection of an event corresponding to a risk, checking the event against a minimum cut set of vulnerabilities, wherein the minimum cut set of vulnerabilities is the smallest set of individual component faults required to trigger a root-level fault, determining a set of resources vulnerable to the risk and, based thereon, taking an action, wherein a resource is a physical or logical capability managed by the operating system.

13. The method of claim 12, wherein the action is issuing an alert to a supervisory node responsible for the determined set of resources.

14. The method of claim 12, wherein the action is updating a system-wide computational risk model.

15. The method of claim 12, wherein the system is an endpoint device.

16. The method of claim 15, wherein the system includes an independent sensor associated with each of the user applications.

17. The method of claim 15, wherein the system includes a single sensor responsible for all of the user applications.

18. The method of claim 12, wherein the system is a server hosting user application for multiple endpoint devices and users.

19. The method of claim 18, wherein the system includes an independent sensor associated with each of the user applications.

20. The method of claim 19, wherein each of the user applications is hosted for multiple simultaneous user sessions.

21. The method of claim 18, wherein the system includes a single sensor responsible for all of the user applications.

22. The method of claim 12, wherein the map identifies dependent system resources requested by the applications and security controls that govern read/write access to such dependent system resources.

* * * * *